May 19, 1942. F. H. HOWARD Plant Pat. 516
ROSE
Filed Nov. 18, 1941
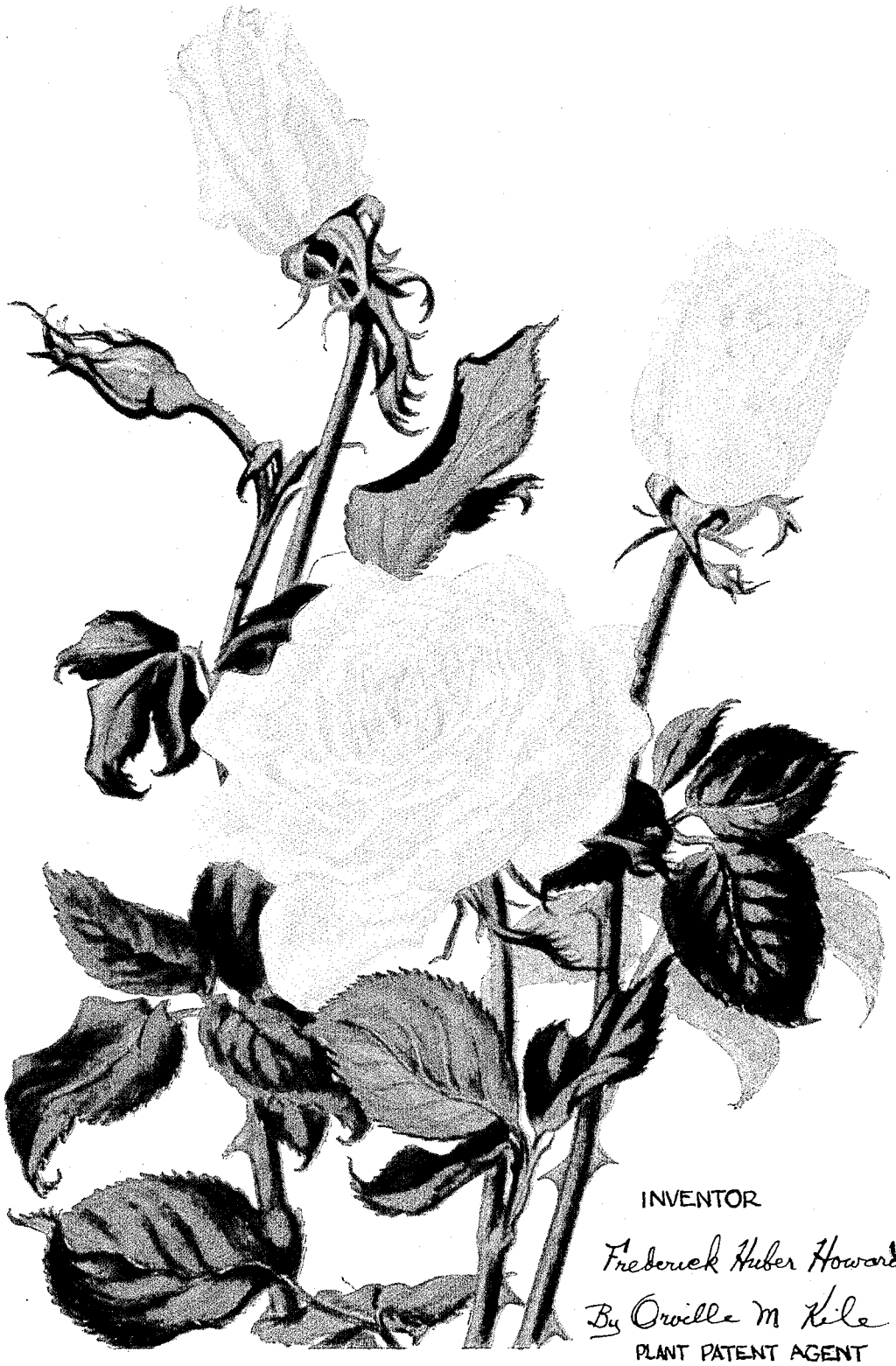
INVENTOR
Frederick Huber Howard
By Orville M Kile
PLANT PATENT AGENT Patented May 19, 1942

Plant Pat. 516

UNITED STATES PATENT OFFICE

516

ROSE

Frederick Huber Howard, Montebello, Calif., assignor to Lester C. Lovett, Red Bank, N. J.

Application November 18, 1941, Serial No. 419,642

1 Claim. (Cl. 47—61)

My new invention relates to improvements in pink hybrid tea rose plants and pertains particularly to the strong, healthy growth of the plant. Probably the most outstanding feature of the variety is its ability to produce a high percentage of good plants when asexually reproduced. Seventy-five percent No. 1 plants result from the cuttings, as compared with the usual fifty percent.

The new variety originated as a result of a controlled cross between an unnamed seedling and the variety Pechtold. It is somewhat similar to its parent in color of blossoms but is decidedly different in its type of growth and its health and vigor. The general character of its growth is more like that of Talisman. It is an exceptionally free bloomer, and has very strong stems and healthy foliage. It is primarily a garden rose but could also be successfully used as a greenhouse rose.

The original illustrations making up a part of this application show a typical field-grown summer blossom and two buds in different stages of opening, and some of the foliage and stems—all in approximately their true colors. It must be understood, however, that some variations occur.

A detailed description of the variety is given below. Color plate references indicate Ridgway's Color Standards and Nomenclature.

*The plant*

Growth: Upright bush. Exceptionally healthy and strong.

Foliage: Disease-resistant and abundant; good all the way to ground; mostly five leaflets, sometimes three.

*Color.*—Dark green, approximately Dark Cress Green (Plate XXXI) on the upper surface and Light Hellebore Green (Plate XVII) on under surface.

*Appearance.*—Glossy on upper surface; smooth.

*Size.*—Varies greatly. Terminal leaflets measure from 1¾ to 2¼ inches by 1¼ to 1¾ inches. Lateral leaflets much smaller.

*Shape.*—Oval, with small sharp apex and rounded base.

*Sepals.*—Five; long; branched; one or two usually somewhat foliaceous; extend far beyond end of bud as color begins to show.

Stems: Very strong; stiff; straight; heavy.

*Internodes.*—Short, permitting leaves to appear close together on stem.

*Thorns.*—Numerous; very sharp; medium to large; irregularly placed; slightly downward-pointing; light green in color, usually with slight reddish tinge.

*The flower*

Bud:

*Color.*—Light delicate pink, varying and shading from Hermosa Pink (Plate I) to Alzarine Pink (Plate XIII).

*Shape.*—Long and slender.

*Size.*—Approximately 3 inches long just before expanding.

Blossom:

*Shape.*—When the bud begins to spread the flower appears deep and loose. But the inner petals are very much shorter and smaller than the outer petals and have an imbricated arrangement, particularly evident in the cool weather flowers.

*Size.*—Medium, averaging 3½ to 4 inches across.

*Color.*—The color is a light pink although the intensity of it varies greatly as between specimens. The majority of the blossoms range from Hermosa Pink to Alzarine Pink on the outer surface and slightly lighter on the inner surface. This color is rather evenly spread over the petal surface except that it diminishes at the edges and there is also a slight yellow aiglet.

*Petalage.*—The number of petals varies considerably. Including the small petaloids found at the center of the blossom, the petalage ranges from 35 to 45 during the summer months and slightly higher in cooler weather.

Reproductive organs:

*Pistils.*—Numerous; tightly bunched in center of flower and partly enclosed in calyx tube; uneven in length. *Style*—very slender; longer than filaments; white; protruding portion usually Rose Red (Plate XII). *Stigma*—small; whitish-green, sometimes slightly red-tinged.

*Stamens.*—Many, surround pistils. *Filaments*—uneven in length; approximately Empire Yellow (Plate IV). *Anthers*—large; attached loosely at one end; Light Cadmium (Plate IV) to Yellow Ochre (Plate XV).

*Calyx cup.*—Large; funnel-shaped.

Having thus disclosed my invention, I claim:

The new and useful variety of hybrid tea rose plant herein described and shown, characterized particularly by its delicate pink blossoms; its very strong, healthy, abundant foliage; its strong, upright stems; its vigorous growth; and its ability, when asexually reproduced, to yield a much higher than average proportion of first class plants.

FREDERICK HUBER HOWARD.